United States Patent
Schilling et al.

(10) Patent No.: US 7,426,324 B2
(45) Date of Patent: Sep. 16, 2008

(54) OPTICAL ROTATING DATA TRANSMISSION SYSTEM WITH A CLEANING DEVICE

(75) Inventors: Harry Schilling, Eichstaett (DE); Thomas Tartler, Moorenweis (DE); Hans Thiele, Munich (DE); Georg Lohr, Eichenau (DE); Rainer Hutterer, Munich (DE); Matthias Rank, Wilmering (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 146 days.

(21) Appl. No.: 11/229,017

(22) Filed: Sep. 16, 2005

(65) Prior Publication Data

US 2006/0067615 A1    Mar. 30, 2006

(30) Foreign Application Priority Data

| Sep. 24, 2004 | (DE) | .................. | 10 2004 046 774 |
| Sep. 24, 2004 | (DE) | .................. | 10 2004 046 775 |
| Sep. 24, 2004 | (DE) | .................. | 10 2004 046 777 |
| Dec. 2, 2004 | (DE) | .................. | 10 2004 058 291 |
| Dec. 2, 2004 | (DE) | .................. | 10 2004 058 292 |
| Dec. 2, 2004 | (DE) | .................. | 10 2004 058 293 |

(51) Int. Cl.
   *G02B 6/26* (2006.01)
(52) U.S. Cl. .............. 385/25; 385/27; 385/32
(58) Field of Classification Search .......... 385/25, 385/27
   See application file for complete search history.

(56) References Cited

U.S. PATENT DOCUMENTS 4,900,117 A   2/1990  Chen 5,031,986 A * 7/1991 Mori ..................... 385/25
6,151,283 A * 11/2000 Kobayashi ............... 369/71
2005/0162119 A1* 7/2005 Landry et al. ............ 318/580

FOREIGN PATENT DOCUMENTS

| DE | 3704887    | 8/1987  |
| DE | 10256634   | 2/2003  |
| DE | 10240228   | 12/2003 |
| DE | 10336925   | 3/2005  |
| EP | 0545950    | 6/1993  |
| WO | 98/14810   | 4/1998  |
| WO | 03/069392  | 8/2003  |

* cited by examiner

*Primary Examiner*—Frank G Font
*Assistant Examiner*—Eric Wong
(74) *Attorney, Agent, or Firm*—Kevin L. Daffer; Daffer McDaniel, LLP

(57) ABSTRACT

An optical transmission system in a computer tomograph for transmitting modulated optical signals between a first unit and a second unit, the first unit being supported to be rotatable relative to the second unit, comprises: a light guide disposed along a circular or annular track on the first unit; at least one first light coupler connected with the light guide for coupling light into or out of the light guide; at least one second light coupler disposed on the second unit to be movable relative to the light guide for coupling light into or out of the light guide. In order to remove from the light guide surface any contaminating matter that would lead to a high signal attenuation or an interference with transmission, a cleaning unit is provided for removing dirt and dust particles. Furthermore, a sealing of the system is provided by applying, amongst other means, pressurized air or electrostatic filtering.

7 Claims, 10 Drawing Sheets

OPTICAL ROTATING DATA TRANSMISSION SYSTEM WITH A CLEANING DEVICE

PRIORITY APPLICATIONS

This application claims priority to the following applications: DE 10 2004 046 774.9 filed Sep. 24, 2004; DE 10 2004 046 775.7 filed Sep. 24, 2004; DE 10 2004 046 777.3 filed Sep. 24, 2004; DE 10 2004 058 291.2 filed Dec. 2, 2004; DE 10 2004 058 292.0 filed Dec. 2, 2004; DE 10 2004 058 293.9 filed Dec. 2, 2004.

BACKGROUND OF THE INVENTION

1. Field of the Invention

The invention relates to an optical rotating data transmission system such as a rotary joint for transmitting optical signals between units rotatable relative to each other. Systems of this kind are preferably used in computer tomographs. The invention also relates to a method for cleaning a surface of the optical transmission system.

2. Description of the Related Art

For transmission of optical signals between units rotatable relative to each other, various systems are known, in particular systems having an unobstructed diameter. With these, a basic problem exists of designing a means for conveying light along the circumference of the system, and also suitable means for coupling light in and out. For use in computer tomographs, systems of this kind must have large unobstructed diameters of the order of magnitude of 1 meter. During rotation, the circumferential speed may be of an order of magnitude of 20 m/s. At the same time, data rates of more than 1 gigabyte per second (Gbaud) should be possible.

Nearly all kinds of optical rotating data transmission systems react sensitively to contamination in the region of the optical signal path. Even in relatively clean surroundings in which, for example, computer tomographs are used, dust particles occur. Thus, for example, in computer tomographs, usually a slip-ring having a brass track and carbon brushes running thereon is used for supplying power supply to an X-ray tube. During operation, these carbon brushes become abraded by sliding on the brass track and thus produce an extremely fine dust that can penetrate into even the smallest of openings. Contamination on the light guide can lead to a high attenuation of signals or an interference with transmission.

A system for wideband signal transmission by means of a light guide divided along a longitudinal direction is disclosed in WO 03/069392. The contents of WO 03/069392 are incorporated in the present document by reference. Here the light guide is exposed and thus unprotected from dust and other contamination.

BRIEF SUMMARY OF THE INVENTION

The invention is based on the object of designing an optical transmission system for transmitting signals between two units rotatable relative to each other, preferably for use in computer tomographs, in such manner that dust and other contamination, in particular of slide-ways, cannot impair the quality of transmission. Another object of the invention is to provide a method for cleaning a surface of a circular light guide of the optical transmission system and for preventing dust and dirt particles from entering the optical system.

In accordance with the invention, the above object is achieved by an optical transmission system in a computer tomograph for transmitting modulated optical signals between a first unit and a second unit, the first unit being supported to be rotatable relative to the second unit, comprising: a light guide disposed along a circular track on the first unit; at least one first light coupler connected with the light guide for coupling light into or out of the light guide; at least one second light coupler disposed on the second unit to be movable relative to the light guide for coupling light into or out of the light guide; wherein at least one cleaning unit is provided for removing contaminating matter from a surface of the light guide.

In accordance with the invention, the above object is also achieved by a method for cleaning a surface of a circular light guide of the optical transmission system of a computer tomograph, comprising the steps of: disposing an automatic cleaning unit to travel along the light guide and remove particles of contaminating matter from the surface of the light guide.

BRIEF DESCRIPTION OF THE DRAWINGS

In the following the invention will be described by way of example, without limitation of the general inventive concept, on examples of embodiment with reference to the drawings.

DETAILED DESCRIPTION OF THE DRAWINGS

Figure 1:
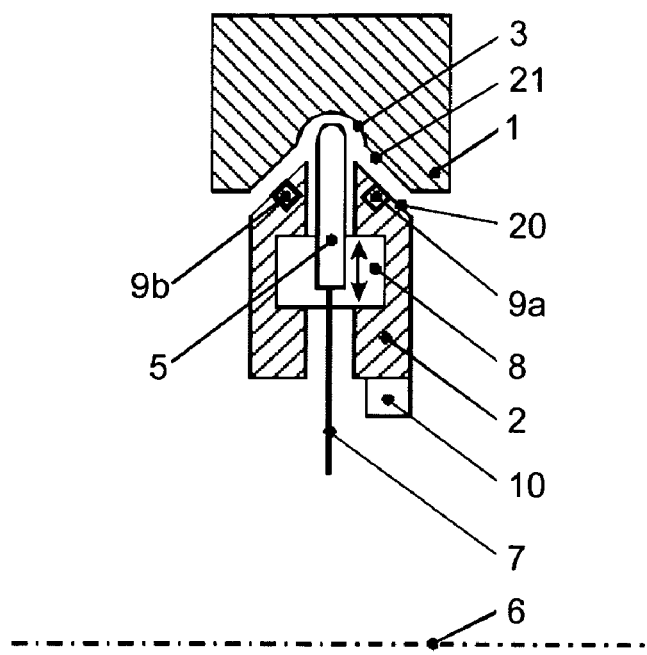
FIG. 1 schematically shows a system according to the invention in a general form.

FIG. 1 shows in a schematic form a cross-section of an optical transmission system according to the invention. In this, a first unit 1 and also a second unit 2 are represented as disks having a central bore, which are supported to be rotatable about an axis of rotation 6. A light guide 3 is here shown by way of example as being a trench that is mirror-coated on an inner side. It extends around the entire circumference of the first unit. A second light coupler 5 disposed on the second unit 2 is in engagement with the trench. This light coupler taps the light guided in the light guide, and relays it by means of a light-guiding fiber 7. A hydrodynamic bearing, and also an electro-dynamic bearing regulation means are provided for an exact alignment of the light guide and the second light coupler along an axis. The hydrodynamic bearing is based on a thin air film formed between a first bearing surface 21 and a second bearing surface 20 by the movement of the two units relative to each other. Support is provided, for example, by additional air-guiding means. An actuator 8 serves for exactly adjusting the height of the light coupler. Sensors 9a and 9b serve for determining contamination.

Figure 2:
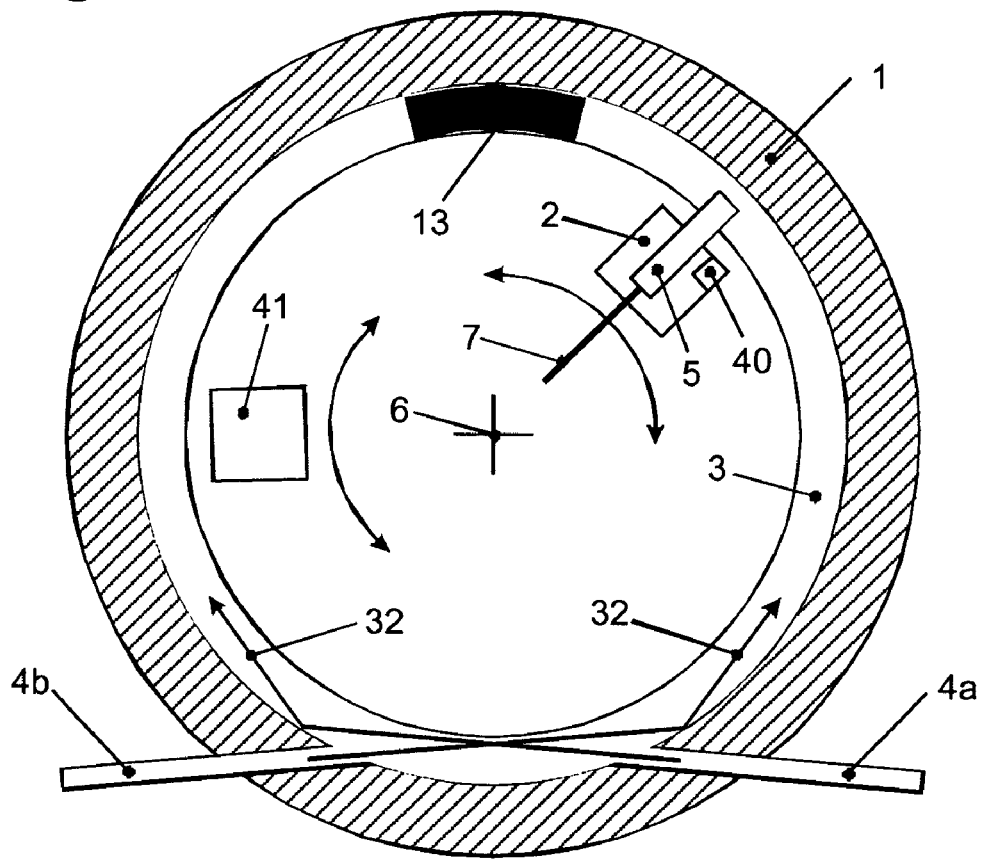
FIG. 2 schematically shows a plan view of a system according to the invention.

FIG. 2 shows in schematic form a plan view of a device according to the invention. A first unit 1 serves to accommodate a circular or annular light guide 3. This light guide is, for example, a trench that is mirror coated on the inside. A second unit 2 rotates relative to the first unit about a rotation axis 6. The second unit comprises a second light coupler 5. Light from a not shown transmitter is fed into the light guide 3 by means of the two first couplers 4a, 4b at the same phase with reference to a modulation signal. The light from the first light coupler 4a travels on the right-hand side of the illustration up to an absorber 13. At the same time, the light from the first light coupler 4b travels on the left-hand side up to an absorber 13. The absorber is disposed symmetrically with reference to a coupling-in position of the first light coupler, so that light paths 32 on both sides are of the same length. Tapping of the light is effected by means of a second light coupler that is supported to be rotatable about the rotation axis 6 along the path of the light guide 3 and conducts the tapped-off light to an optical receiver. For the sake of simplicity, the optical receiver also has not been illustrated. A cleaning unit 40 is incorporated in the second unit 2. Together with this second unit it travels along and suitably cleans the light guide 3. Furthermore, an independent cleaning unit 41 is illustrated which can be moved independently from the second light coupler.

Figure 3:
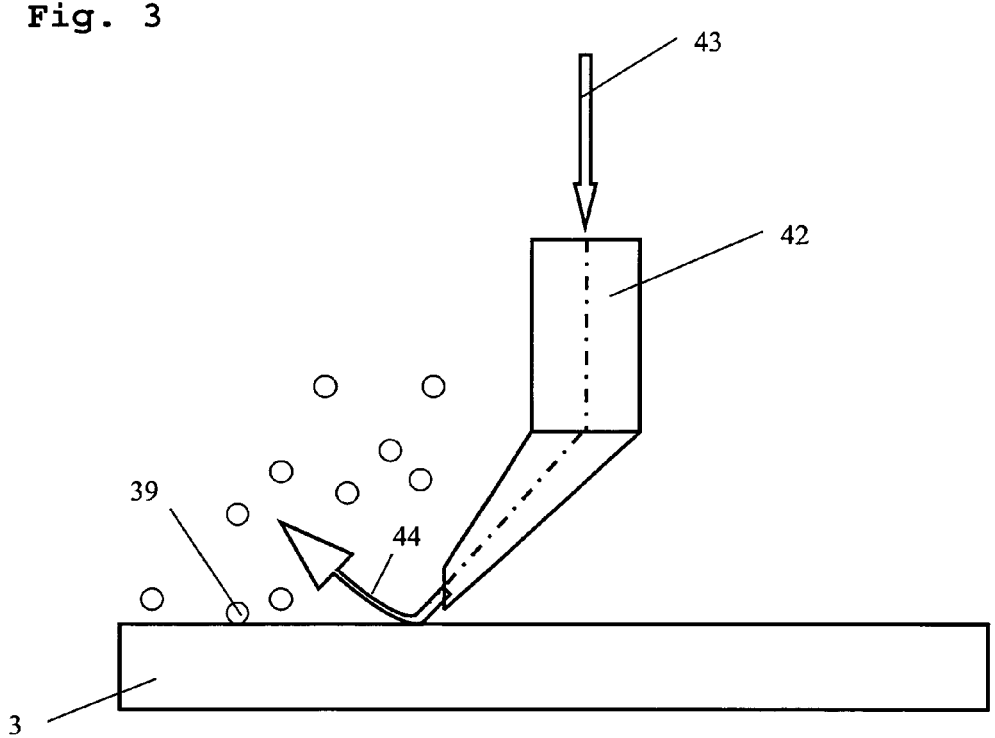
FIG. 3 shows a cleaning unit in the form of an appliance for blowing away dust and dirt particles.

FIG. 3 illustrates a cleaning unit in the form of an appliance for blowing away dust and dirt particles. An air current 43 from a pressurized air source is blown along the direction of the light guide 3 by means of a nozzle 42. An air current 44 issuing from the nozzle causes a swirl of raised dust particles 39 and blows them away from the light guide.

Figure 4:
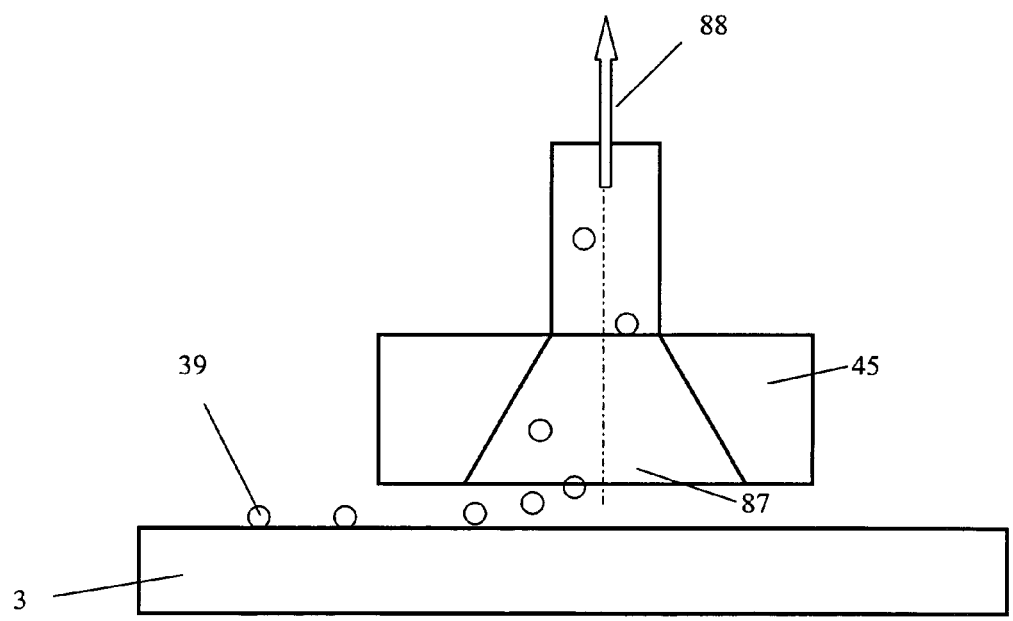
FIG. 4 shows a cleaning unit in the form of a suction appliance.

FIG. 4 shows a cleaning unit in the form of a suction appliance. A nozzle block 45 configured as a nozzle comprises a suction opening 87 through which air is sucked-in from the outside. An air stream 88 entrains the dust particles 39 and thus removes them from the surface of the light guide 3.

Figure 5:
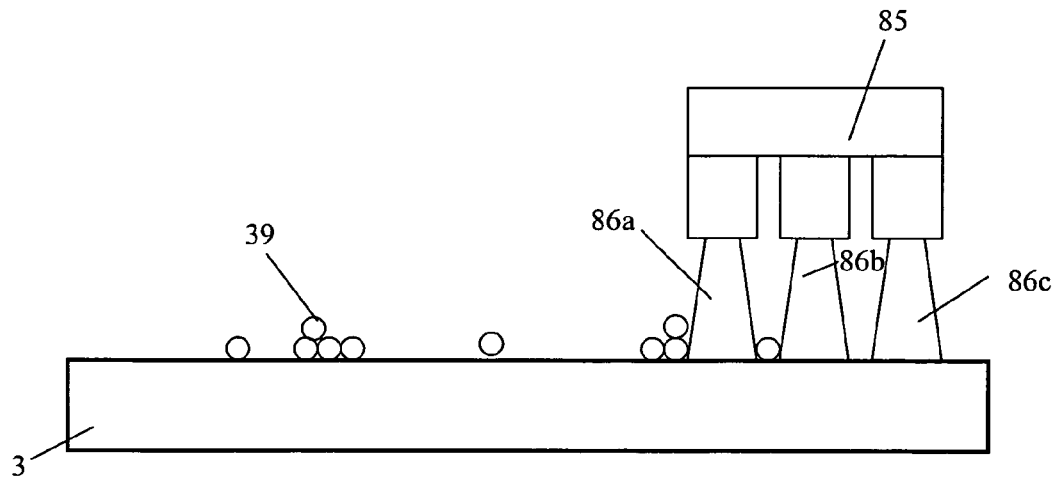
FIG. 5 shows a cleaning unit in the form of a brush unit.

FIG. 5 shows a cleaning unit in the form of a brush unit. A brush holder 85 serves to accommodate brushes 86a, 86b, 86c. The brushes are moved along the light guide 3 and thus sweep away dirt particles deposited on the surface.

Figure 6:
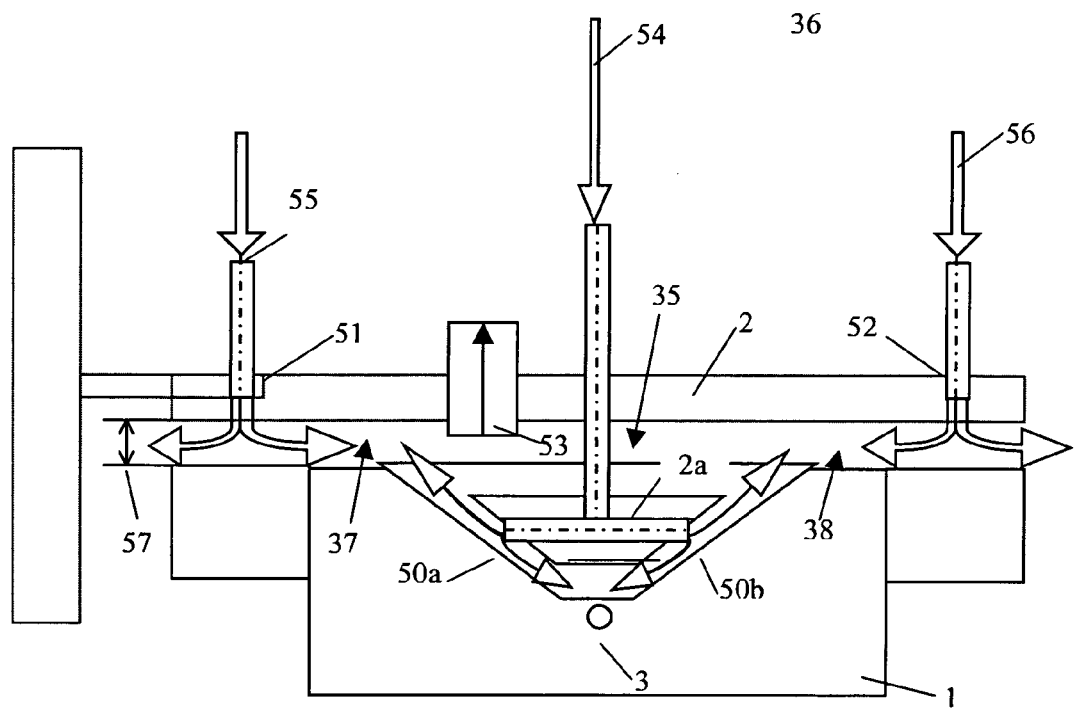
FIG. 6 shows a system according to the invention using seal air as a sealing means.

FIG. 6 shows a system according to the invention using seal air as a sealing means. In this illustration a sliding body 2a connected to the second unit 2 is provided for accommodating the light coupler 5. This sliding body 2a is connected to the second unit 2 so that it performs the same movement along a longitudinal direction of the light guide 3, but effects a stabilization along one or two axes perpendicular thereto, so that an exact alignment of the light coupler 5 on the second unit with respect to the light guide 3 is always ensured. An especially precise support of this sliding body 2a relative to the first unit 1, with low friction at the same time, can be achieved with an air bearing. An air bearing of this kind is illustrated as an especially preferred example for describing the embodiments of the invention. Of course, any other kind of bearing means is possible, such as for example a sliding bearing or a rolling bearing. As an example of an air bearing, two nozzles 50a, 50b are illustrated, from which a supplied air stream 54 is emitted from a not shown pressurized air source in the direction of the first unit 1, in order to build up an air film between the sliding body 2a and the first unit 1. The air introduced through the nozzles flows away laterally between the sliding body 2a and the first unit 1. It can escape from the hollow space shown in the drawing between the components of the first unit 1 and the second unit 2 through the vent valve 53.

For sealing by means of seal air, at least one seal air nozzle 51 is provided for emitting a seal air stream 55 into the space between the first unit 1 and the second unit 2 in such manner that it escapes to the outside from the gap between the two units and thus prevents an entry of dust and other dirt particles into the gap between the two units. For sealing the second side, a second seal air nozzle 52, fed by a seal air stream 56, has been drawn. In order achieve an optimal sealing performance, the gap 57 between the first unit 1 and the second unit 2 can be optimized. Particularly expedient is a gap of an order of magnitude of 0.03 millimeters to 0.1 millimeters, a pressure of 0.2 bar to 0.5 bar in excess of the ambient having proved to be of advantage. The same applies to the gap 58. The exact number of gaps is of no consequence to the subject matter of the invention, because this is usually a question of definition. Thus, for example, the two gaps 57 and 58 may also be regarded as being one single gap between the two units. Essential to the invention is that at least one gap is present between the two units.

Figure 7:
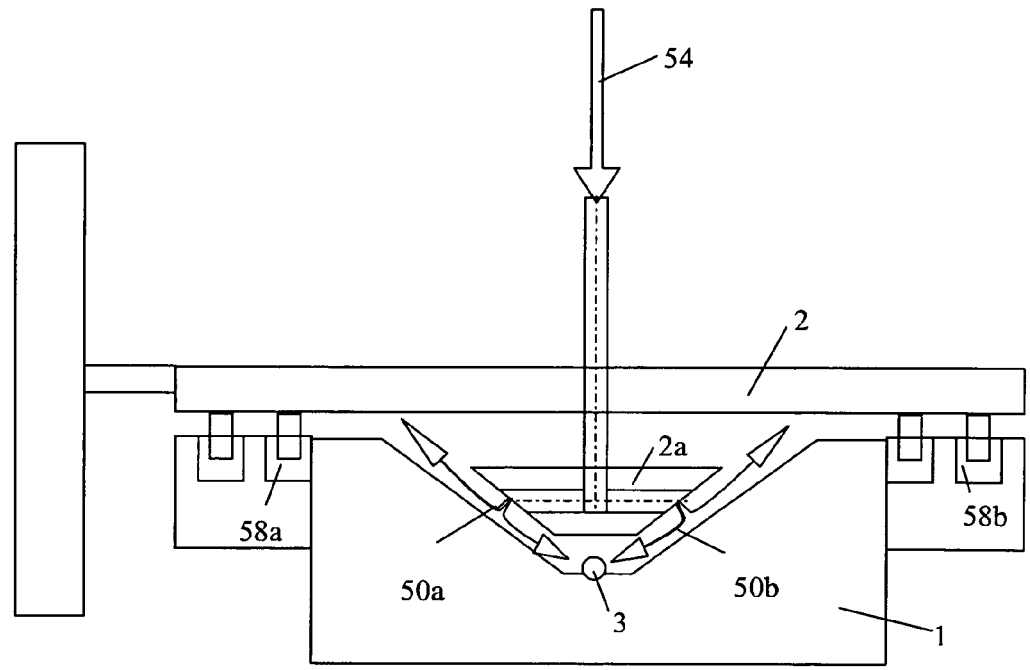
FIG. 7 shows a system according to the invention using a labyrinth sealing means.

FIG. 7 shows a system according to the invention using a labyrinth sealing means. With this, an entry of dust and other foreign bodies into a region sensitive to contamination surrounding the light guide 3 is rendered difficult by a labyrinth. This labyrinth is preferably configured by the design of an interlocking structure of grooves or ribs between the first unit 1 and the second unit 2. In the particular case of embodiment using an air bearing means, as illustrated here, the supplied air stream 54 blown into the hollow space escapes to the outside through the labyrinth after emerging from the bearing means and obstructs any entry of dust. However, a labyrinth sealing means of this kind is capable of operating even without the air stream.

Figure 8:
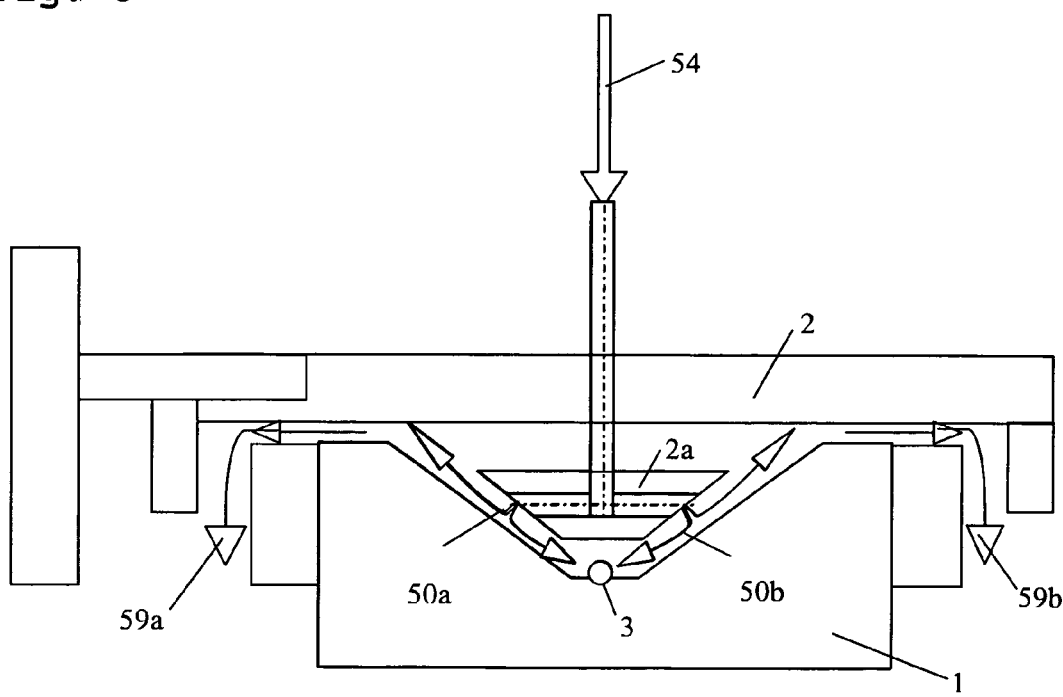
FIG. 8 shows a system according to the invention using excess pressure as sealing means.

FIG. 8 shows a system according to the invention using excess pressure as a sealing means. In a similar manner as in the previous example, an aim is to maintain a continuous air stream 59a or 59b towards the outside, however, with a substantially larger amount of air. As distinct from the case of the labyrinth sealing means, the mechanical design here is substantially more simple, however, without the air stream only a very small sealing action can be expected. However, in many cases of application this need not be regarded as being particularly critical, because in a non-operating condition of a system, the amount of dust whirled upwards from the outside, and with it a risk of contamination, is usually substantially less. An air supply can be effected optionally from the supply to the air bearing means, or by means of additional inlet openings. Preferably a plurality of inlet openings are provided by being distributed along the circumference of the arrangement.

Figure 9:
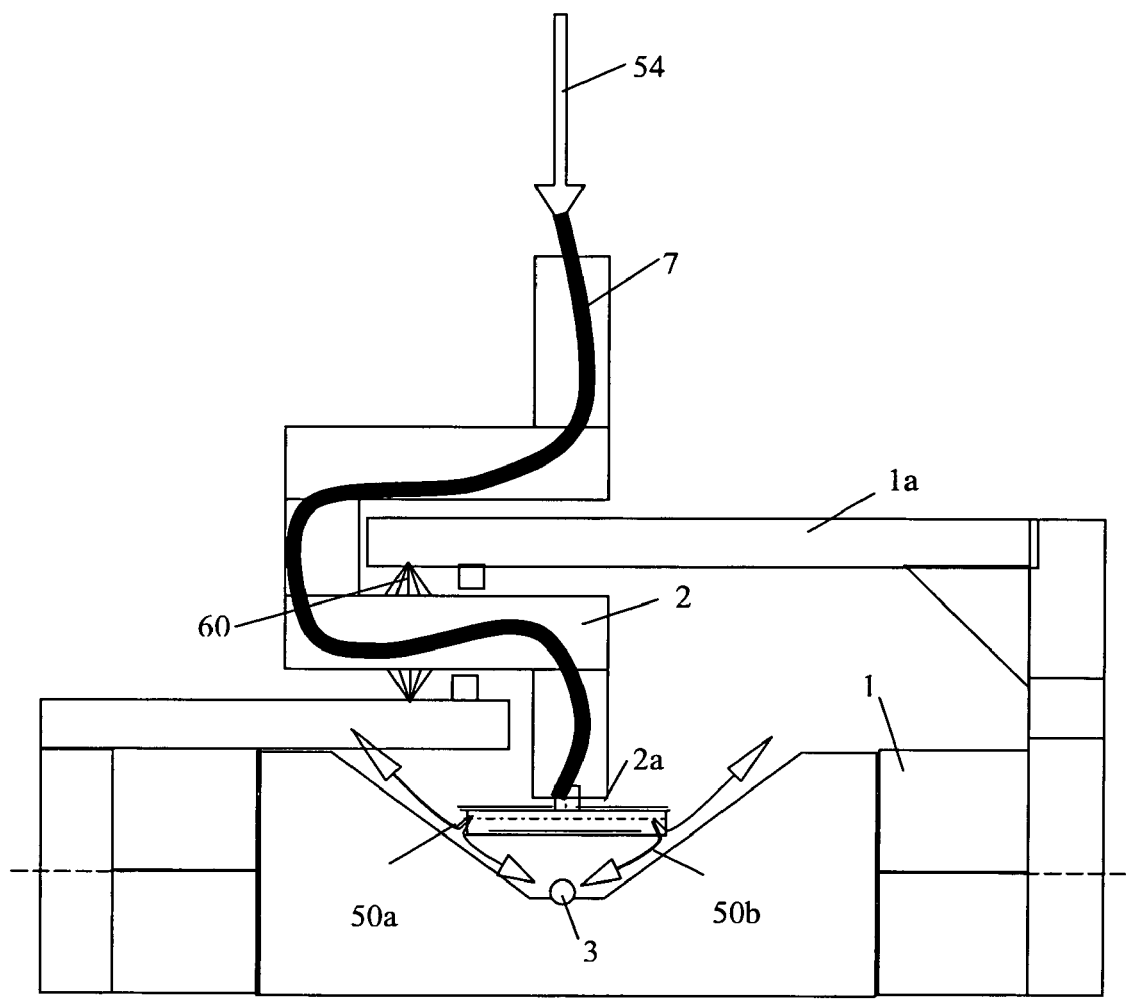
FIG. 9 shows a system according to the invention using a brush sealing means.

FIG. 9 shows a system accordance with the invention using a brush sealing means. In this, brushes 60 are provided for preventing an entry of dust and dirt into the space between the first unit 1 and the second unit 2. In an advantageous manner, additional barriers or labyrinths may be provided for improving the sealing action. In this example of embodiment a fixed cover 1a is provided on the first unit 1, so that only a relatively small region is left for the second unit 2 to allow a passage for a light-guiding fiber 7 and also for the supplied air stream 54 which is needed in this example.

Figure 10:
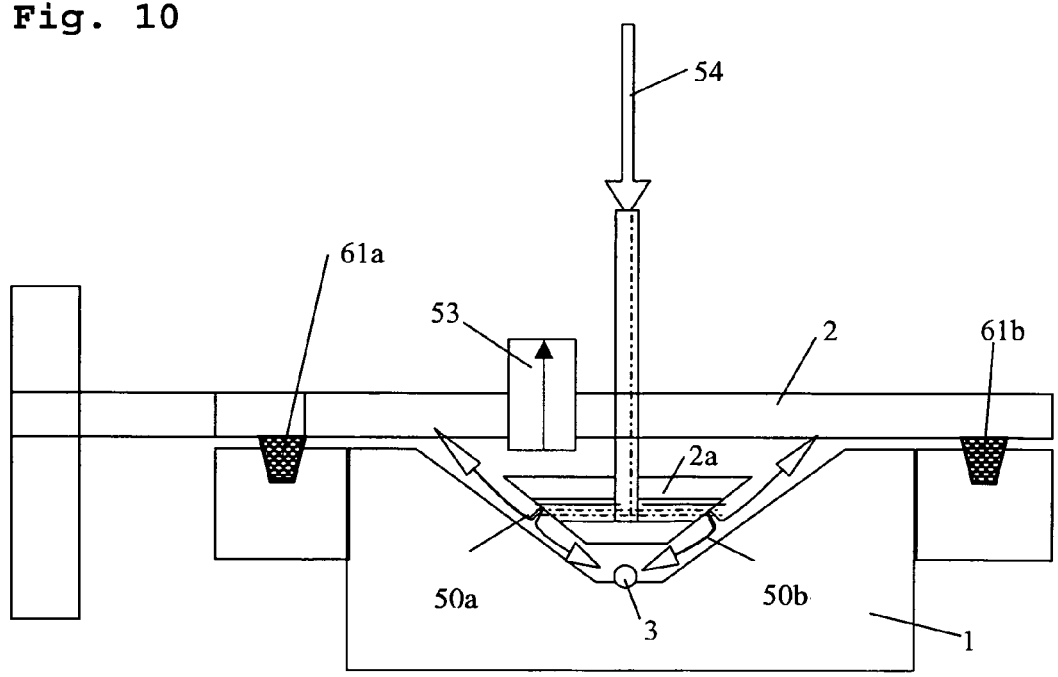
FIG. 10 shows a system according to the invention using a felt sealing means.

FIG. 10 shows a system in accordance with the invention using a felt sealing means. A sealing means of this kind may be configured similarly to the above-described brush sealing means. Here, once again for example, the planar arrangement of the first unit 1 and the second unit 2 is illustrated. Here, the internal excess pressure may also be used to back up the felt sealing means.

Figure 11:
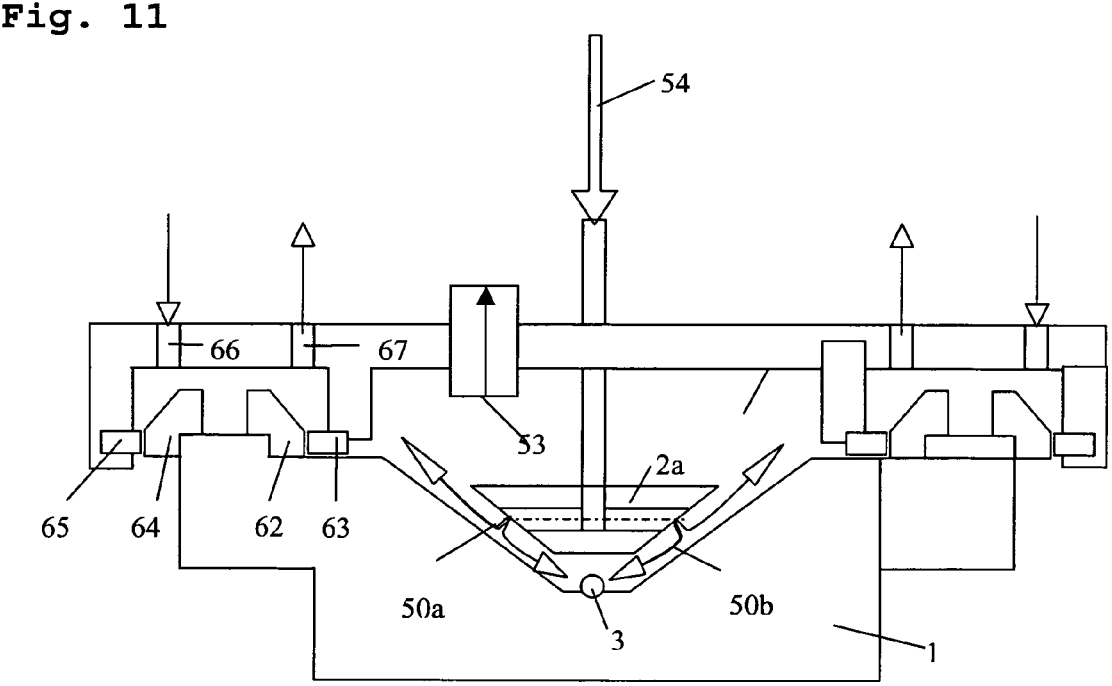
FIG. 11 shows a system according to the invention using a sliding-ring sealing means.

FIG. 11 shows a system according to the invention using a sliding-ring sealing means. Because of the symmetrical construction of the system shown here, reference will be made only to the sliding-ring sealing means shown on the left-hand side of the illustration. Basically, a simple sliding-ring sealing means having a sliding ring 62 and also a counter-ring 63 would already effect a sealing of the inner space. To improve the sealing action, a second sliding ring 64 with an associated counter ring 65 is also provided. Furthermore, seal air or another seal means, such as for example a liquid, is introduced into the intermediate space defined by the two sliding rings and their counter-rings through a seal air inlet 66, and is discharged through a seal air outlet 67.

Figure 12:
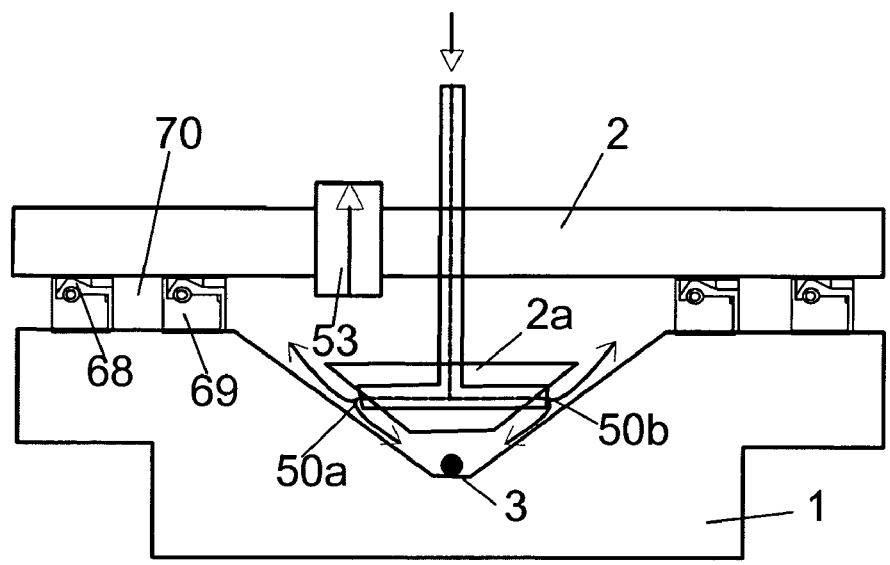
FIG. 12 shows a system according to the invention using a rotary-shaft sealing means.

FIG. 12 shows a system according to the invention using a rotary-shaft sealing means. Here, rotary-shaft sealing rings 68, 69 are provided for sealing the inner space. For example, a lubricant can be introduced into the intermediate space 70 between the rotary-shaft sealing rings. It may be subjected to impingement by seal air in a similar way to that previously illustrated.

Figure 13:
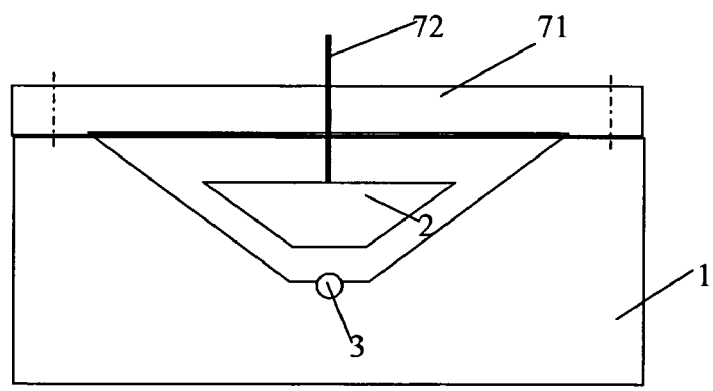
FIG. 13 shows a system according to the invention using a static sealing means.

FIG. 13 shows a system according to the invention using a static sealing means. Here, as distinct from the previously described sealing systems, the space above the light guide 3 is completely sealed statically. For this, a light-transmitting cover 71, such as for example a glass plate or a polymethylmethacrylate plate may be mounted above the light guide. Light is preferably coupled through the light-transmitting cover 71 in the form of a light beam 72 that can be freely positioned. A sliding body 2a assigned to the second unit 2 and containing the optical elements needed for coupling with the light guide 3 may be mechanically coupled with the second unit 2, for example with magnetic take-up means.

Figure 14:
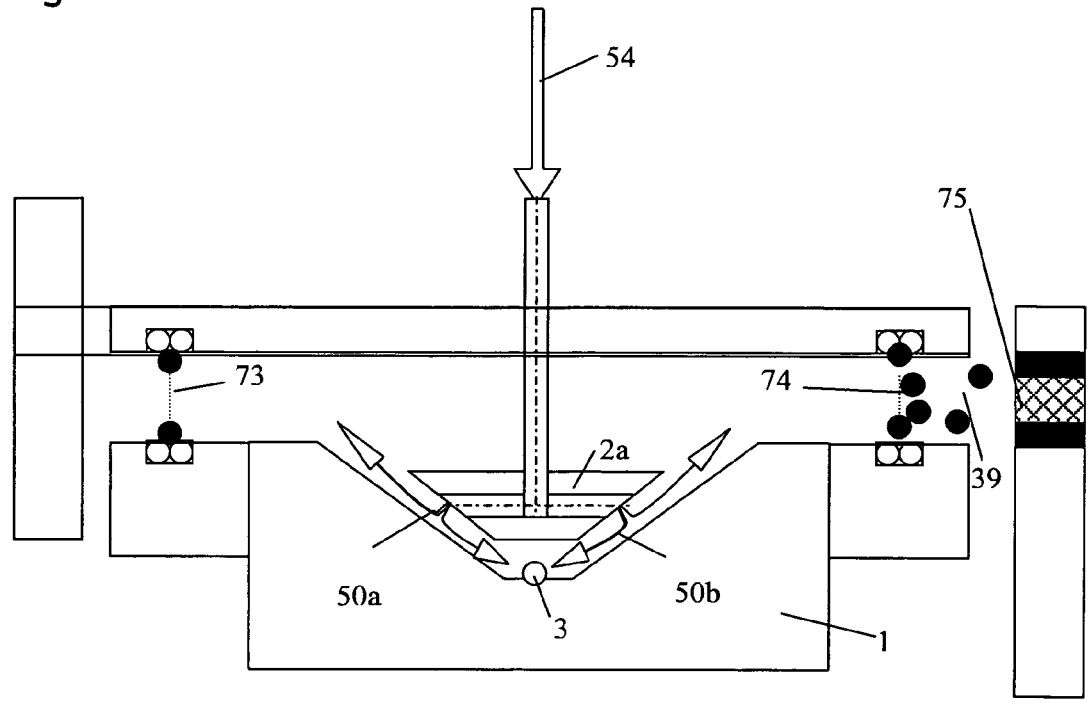
FIG. 14 shows a system according to the invention using a mechanical filter.

FIG. 14 shows a system according to the invention using a mechanical filter. Here a mechanical filter 73 or 74 is provided in order to prevent an entry of dust or dirt particles into the intermediate space between the first unit 1 and the second unit 2. A gauze, for example, may be used as a filter material. By way of supplementation, a further filter 75 having a larger surface, for example an expanding-bellows type filter, may be employed. With this, rapid clogging of the filter may be prevented or delayed. Additional support for the filter action, or cleaning of the filter, can be effected by means of the supplied air stream 54 from the inside.

Figure 15:
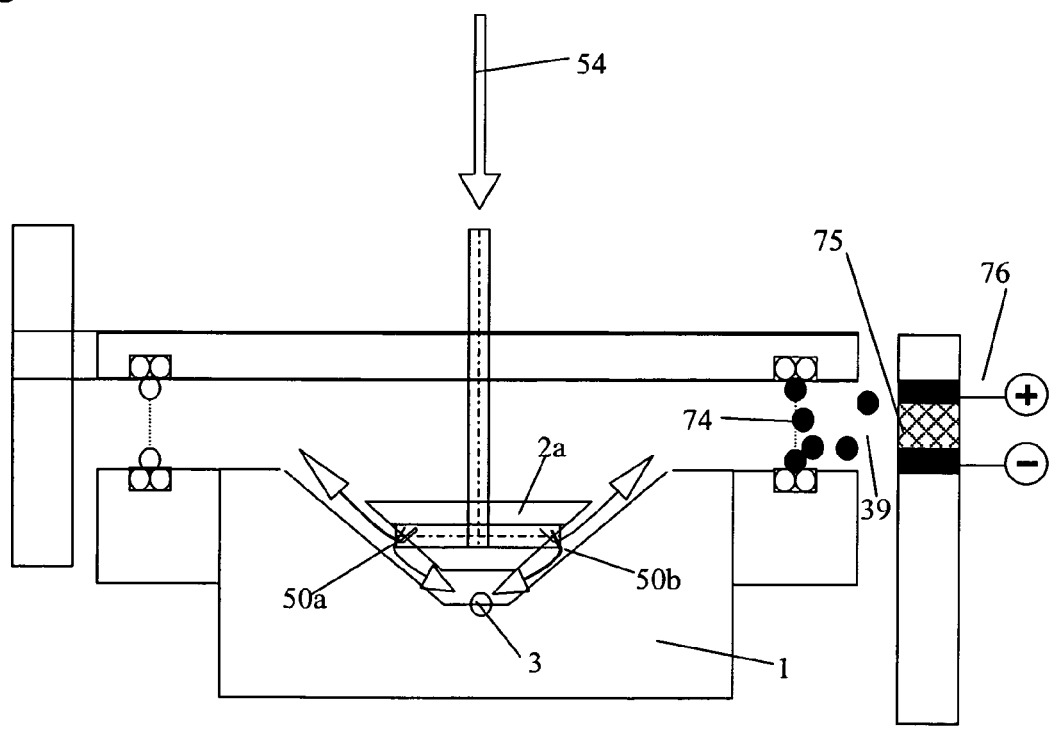
FIG. 15 shows a system according to the invention using an electrostatic filter.

FIG. 15 shows a system according to the invention using an electrostatic filter. This is basically built up similarly to the previously described system with the mechanical filter. However, here an electrostatic filter is optionally employed instead of the mechanical filter 73, 74 or the gauze, or also instead of the additional filter 75. The power supply for this electrostatic filter is effected via high-tension terminals 76.

Figure 16:
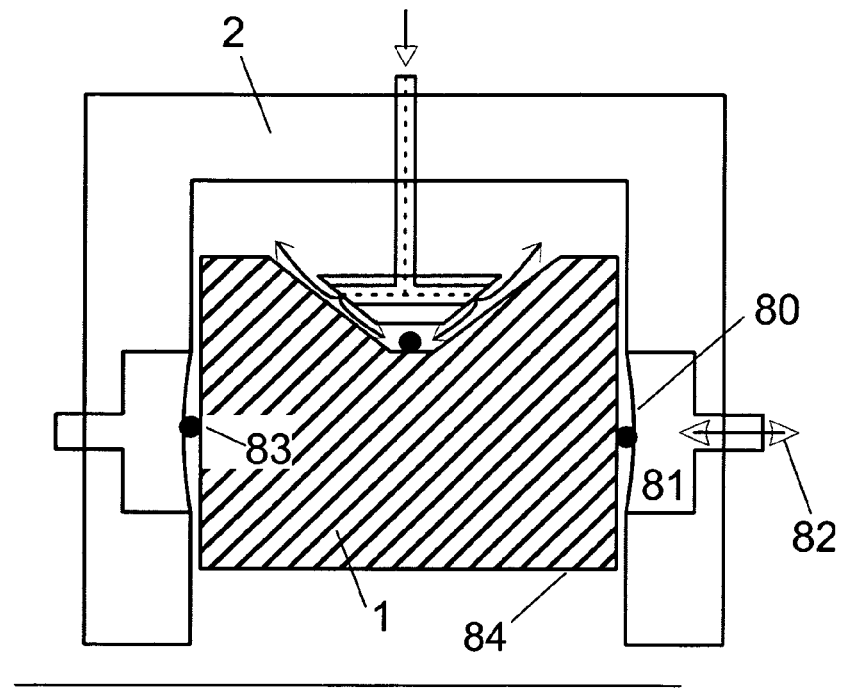
FIG. 16 shows a system according to the invention using a diaphragm sealing means.

FIG. 16 shows an arrangement using a diaphragm sealing means. In this, a sealing diaphragm 80 is provided and disposed in front of a hollow space 31. The position of the sealing diaphragm can now be changed by means of vacuum or pressurized air 82. In the shown illustration it may be urged against the seal 83 of the first unit by being impacted by pressurized air, and lifted off by the action of vacuum. The gap clearance 84 indicates the lift of the sealing diaphragm. In the illustrated embodiment the diaphragm is so dimensioned that in a rest condition when subjected to no load it just rests against the sealing ring. With this, a certain minimum sealing action is ensured, even in the rest condition. To increase the sealing action, the hollow space or the reverse side of the diaphragm may now the subjected to impingement by excess pressure. During operation, the air is removed from the hollow space by vacuum, so that the sealing diaphragm is lifted off from the seal and operation is possible with a minimum of friction.

Figure 17:
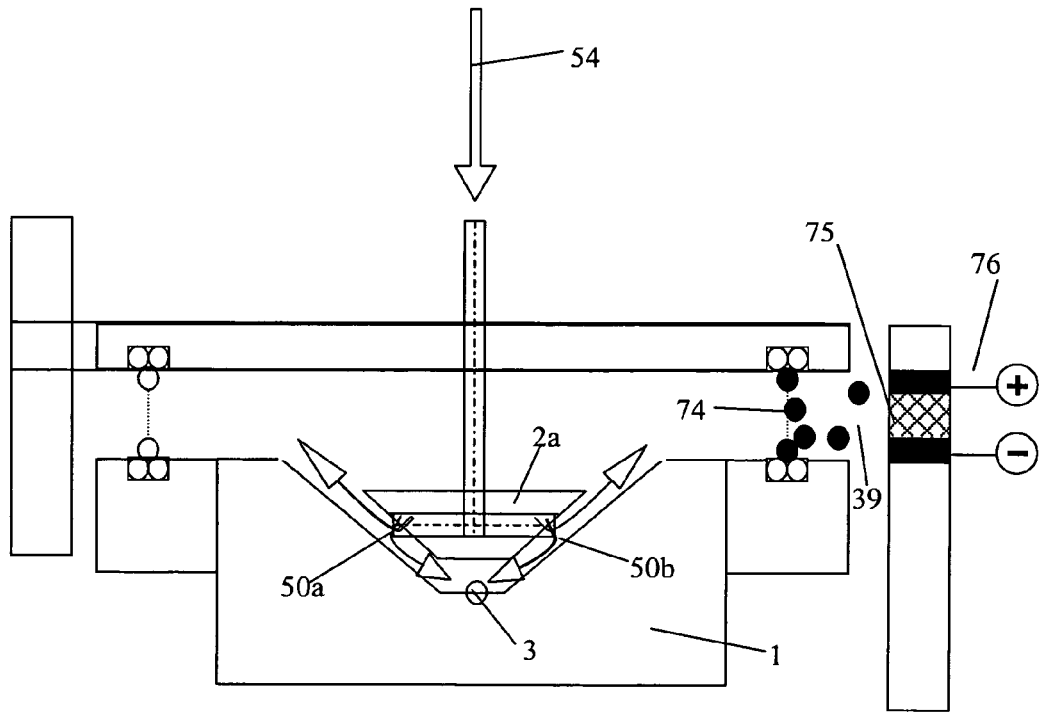
FIG. 17 shows a system according to the invention using a laterally disposed electrostatic filter.

FIG. 17 shows a system according to the invention using a laterally disposed electrostatic filter. The supplied air stream 54 flowing out through the nozzles 50a and 50b into the sliding body 2a of the second unit 2 and forming the air film needed for the air bearing generates an outwardly directed stream from the bearing region. The dust and dirt particles 39 entrained by this stream are filtered away by an electrostatic filter 75. The filter 75 is an additional filter of gauze for protecting the inner region of the bearing from entry of dust and dirt. The electrostatic filter 75 is supplied with power via the voltage terminals 76. The supply may also be effected by providing a high-voltage line-unit or a device for generating a high voltage by electrostatic charging, for example with frictional electricity caused by the movement of the first and the second unit relative to each other.

Figure 18:
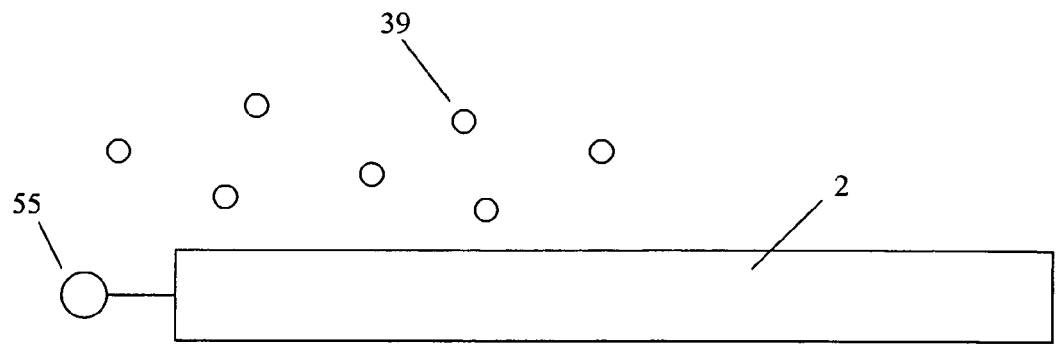
FIG. 18 shows a system according to the invention for repelling charged dust and dirt particles.

FIG. 18 shows another kind of electrostatic cleaning of the surface, in particular that of the second unit 2. For this, it is subjected to high voltage with a static voltage supply 90, to repel charged dust and dirt particles 39. An additional surface of opposite polarity may be provided to then attract and also retain these particles. For this, the surface may be provided with a coating, preferably of a polymer having a high adhesion.

Figure 19:
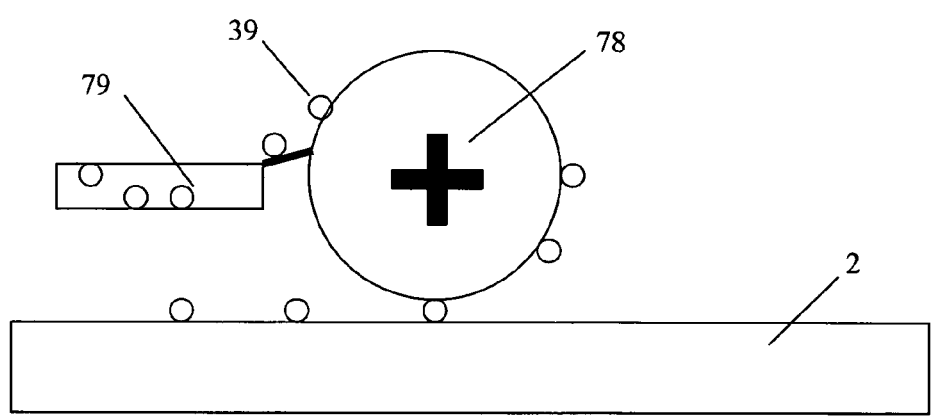
FIG. 19 shows a system according to the invention using a roller for taking-up charged dust and dirt particles.

FIG. 19 shows a system according to the invention using a roller for taking-up charged dust and dirt particles. For this, a roller 78 that is charged, for example by means of a voltage supply, is moved close to and along the surface to be cleaned, preferably that of the second unit. This now takes-up charged dust and dirt particles. In order for a non-contaminated surface of the roller to be always available, it is moved along whilst in rotary movement. In the present example, the direction of rotation is counter-clockwise. Furthermore, a collector 79 is provided for stripping the dust and dirt particles from the roller. The surface of the roller may be variously configured. Thus, the roller may be provided with a continuous conducting surface which is fed in its entirety from a high voltage supply. It also may be configured similarly to known photoconductive drums in photocopying apparatus or laser printers, the charging of the surface being effected from a corona electrode disposed in the vicinity of the surface.

Furthermore, a combined micro-/nanocoating can be used for preventing particles 39 (FIGS. 18-19) from depositing on the surface by means of an effect as known from a lotus blossom. A structure of this kind can be mounted optionally on the first unit 1, or the second unit 2, or on other parts such as the light guide. For this, preferably a microstructure having portions with elevations in a micrometer range is combined with an overlying nanostructure having portions with elevations in a nanometer range. A surface coated in this manner can now be configured, for example, so that contamination can be completely blown away from the critical regions of the surface (optical components). Similarly, it may be specifically directed into a collecting container, or into a collecting filter.

Of course, the various embodiments of the invention described here may be combined in order to achieve better filtering of dirt and dust particles.

DETAILED DESCRIPTION OF THE PREFERRED EMBODIMENTS

An optical rotating data transmission system in accordance with the invention comprises a light guide 3 disposed on a first unit 1 along a circular track. For the sake of simplicity, only one light guide is described here. Of course, a plurality of light guides also may be provided in a system according to the invention. For tapping signals from the light guide 3, a light coupler 5 is provided on a second unit 2 that is supported to be rotatable relative to the first unit 1. Furthermore, a cleaning unit 40, 41 is provided for removing dirt and/or dust particles from the light guide 3. It is the primary purpose of the cleaning unit to remove contamination from the light guide 3. Of course, contamination may be removed also from surrounding components such as a bearing assembly, in particular an air-bearing assembly.

In another embodiment of the invention, at least one cleaning unit 40 is mounted to at least one second unit 2 to move together with the second unit 2 along the light guide 3. Thus, the cleaning unit travels together with a movement of the second unit. Thereby a simple design of a supporting and driving structure for the cleaning unit 40 may be achieved. It is particularly expedient for the cleaning unit to be directed along the direction of movement ahead of a light coupler 5, so that the light guide may be cleaned before a transmission. On the other hand, with embodiments using liquid cleaning means, it may be of particular advantage to direct the cleaning unit to follow behind a light coupler 5 along the direction of movement, because then any cleaning fluid remaining on the light guide may dry.

Another embodiment of the invention provides a cleaning unit 41 that is movable along a light guide 3 independently from a second unit. With this embodiment, control of travel of the cleaning unit 41 can be made independently from the movement of a light coupler 5. Thus, both may be moved at different speeds, in order to achieve, for example, a conforming of the speed to the amount of contaminating matter. Accordingly, also a plurality of cleaning appliances may be provided to move along the light guide at fixed distances, or also independently from each other. According to the design of the cleaning unit 41, the movement may be along the same track as that of a light coupler 5. With this, it is not possible for a cleaning unit 41 to overtake a light coupler 5. Nevertheless, the local speed of the cleaning unit 41 may be conformed. Thus, for example, it may be reduced at a particularly heavily contaminated location, and at least briefly increased following a cleaning of this location, in order to prevent a collision with a light coupler 5. Alternatively, a cleaning unit 41 also may be designed so that it uses a different track than a light coupler 5. Here, a cleaning unit 41 of this kind may be moved completely independently from a light coupler 5. For this, the cleaning unit 41 is preferably disposed laterally or above the track of the light coupler 5.

Another embodiment of the invention provides a sensor for detecting contamination. Furthermore, a control unit 10 is optionally provided for adjusting the operating time and/or the intensity of cleaning of the cleaning unit in dependence upon the extent of contamination. Thus, for example, in the case of particularly heavy contamination, cleaning can be performed at a higher pressure, or at a higher temperature, or with a larger amount of cleaning fluid, whilst for example in the case of very small or no detectable contamination, the cleaning unit can switched off. Thereby a low consumption of energy and also, as the case may be, a low consumption of cleaning agents may be achieved.

An advantageous embodiment of the invention provides a cleaning unit in the form of an appliance for blowing-away dust and particles of dirt. For this, preferably air in an air stream 44 is blown onto the light guide 3 with a nozzle 42. Of course, apart from air, other gases and even liquids are suitable. A source of pressurized air, or an air pump, is provided for supplying the nozzle with an air stream 43. The dust or dirt particles are whirled upwards from the surface of the light guide 3 and carried away by the air stream. It is of particular advantage to dispose the nozzle so that the particles whirled upwards are blown away to a side the light guide 3. For this, air-guiding devices such as air-guiding plates may be provided to promote this effect. Advantageously the air pump has a filter, so that only cleaned air is blown onto the light guide. Another improvement of the cleaning action may be achieved by generating vortices having a high locally confined streaming velocity at the surface of the light guide. For this, it may be of advantage to direct an air current 44 counter to the direction of movement of the cleaning unit.

For applications in which an air bearing is provided for supporting a light coupler 5 with respect to the light guide 3, an air stream for blowing away particles of dust and dirt can be generated from pressurized air ducts that are provided for conveying the air that is in any case required for the bearing.

In another advantageous embodiment of the invention, a cleaning unit 40, 41 comprises a suction appliance. A suction appliance of this kind is connected to a source of sub-atmospheric pressure such as an air pump. It has a suction opening 87 through which air is sucked away from the surface of the light guide 3. This suction opening is preferably disposed so that it produces as high as possible a streaming speed at least within a narrow area above the surface of the light guide. This streaming speed should be dimensioned to be so high that a large proportion of dirt particles are swept up. In advantageous manner a filter is also provided in the air stream for holding back the particles of dust and dirt, so that they are not discharged into the surrounding air. A suction appliance of this kind may be very advantageously combined with the above-described blowing-away appliance. In this case it may be sufficient for the appliance for blowing away to generate an air stream of a high speed. This suction appliance then need only remove the swirling particles, but requires no high streaming speed for this.

Another advantageous embodiment of the invention provides a brush unit for cleaning the surface of the light guide. This brush unit typically comprises a brush holder 85 for accommodating one or more brushes 86a, 86b, 86c. The brushes are disposed so that they slide along the surface of the light guide 3. The brushes may be configured like paintbrushes, but also may have the shape of a roller. Advantageously several brushes are disposed in succession along the direction of movement in order to achieve particularly thorough cleaning. Furthermore, brushes of different hardness may be combined with each other in order to remove various particle sizes of different contamination from the light guide 3. Here too, a combination of a brush unit with the previously described suction appliance and/or the previously described blowing-away appliance is of special advantage. Hereby a substantially stronger cleaning action can be achieved than with only one of these devices.

In a method according to the invention, the cleaning of a surface of the light guide 3 is effected in the above-described system for transmitting optical signals by generating an air stream 44 with a nozzle 42 and blowing away dust and dirt particles from the surface of the light guide 3.

Another method in accordance with the invention for cleaning the surface of the light guide 3 comprises a sucking-away of dust particles and dirt particles from the surface of the light guide 3.

Another method in accordance with the invention for cleaning the surface of the light guide 3 comprises a brushing-away of dust particles and dirt particles from the surface of the light guide 3.

Another method in accordance with the invention for cleaning the surface of the light guide 3 comprises an emission of a stream of a vapor 56 such as steam that is directed onto the light guide 3.

Another method in accordance with the invention for cleaning the surface of the light guide 3 comprises an application of a cleaning fluid 48 onto the light guide 3, and also a taking-up of the cleaning fluid 48 together with the dirt particles 39 dissolved therein.

Another system according to the invention comprises an optical rotating data transmission device having a light guide 3 disposed along a circular track on a first unit 1. For the sake of simplicity, only one light guide is described here. Of course, a plurality of light guides may also be provided in a system according to the invention. For tapping-off signals from the light guide 3, a light coupler 5 is provided on a second unit 2 that is supported to be rotatable relative to the first unit 1. The first unit 1 and the second unit 2 are designed so that they jointly surround at least one light guide 3. An inner region 35 is defined in the surrounded space containing the light guide 3. An outer region 36 is present outside the entire arrangement. Gaps 37, 38 necessitated by the rotatable arrangement of the two units relative to each other extend between the inner region and the outer region. Furthermore, a device is provided for separating the inner region from the outer region. This device is configured so that an entry of dirt and/or dust particles from the outer region into the inner region is rendered difficult or prevented. It preferably operates in a hydrodynamic manner.

In an especially advantageous embodiment of the invention, this hydrodynamic device is supplied with air that has already been used for operating a hydrostatic or hydrodynamic bearing, in particular an air bearing.

In another advantageous embodiment of the invention, additional seal air 55 is blown into the gaps 37 and 38 through at least one seal air nozzle 51, 52. This seal air provides at least an air stream that passes from the inner region into the outer region, and renders difficult an entry of interfering particles. For an attainment of an optimal effect, the height 57 of a gap 37 should be within a range of 0.03 to 0.1 mm. Especially advantageous is a height of an order of magnitude of 0.6 mm. A pressure of the seal air 55 of 0.2 to 0.5 bar at the place of ejection from the seal air nozzle has proved to be of advantage. For discharge of the amounts of the seal air passing to the inside, and the supplied air stream 54, a vent valve 53 is advantageously provided. For an improved distribution of the seal air along the circumference of the arrangement, it is of advantage to provide additional annular grooves in the vicinity of at least one gap 37 or 38. Similarly, it is of advantage to feed in the seal air at several positions, preferably along the circular circumference. It is of special advantage to use seal air to seal-off both gaps 37 and 38 from an entry of dirt and dust.

Another advantageous embodiment of the invention provides at least one labyrinth sealing means 58a, 58b in the vicinity of the gaps 37 or 38. To configure the labyrinth sealing means, the first unit and also the second unit comprise recesses such as annular grooves, and protrusions such as ribs intermeshing therewith, in the vicinity of the gaps. It is essential for the protrusions and recesses to intermesh with each other. This increases the path length between the outer region and the inner region. Furthermore, the flow resistance is increased. A design having sharp edges causes additional vortices that lead to contaminating matter being deposited within the labyrinth before it can penetrate into the inner space. Owing to the increase of the flow resistance, a smaller quantity of air is sufficient for supplying the inner region with seal air.

Another embodiment of the invention provides brushes 60 between the inner region and the outer region in the vicinity of the gaps. This enables a relatively good sealing action to be achieved, particularly in combination with narrow gaps or labyrinths. This embodiment also permits protection of the inner region during non-operation and without air being supplied. Dust and dirt collected on the brushes can be blown away outwards by a higher air-pressure.

In another embodiment of the invention, a felt sealing means, for example in the form of a felt ring 61a, 61b, is provided between the inner region and the outer region in the vicinity of the gap. This too results in an especially good sealing effect which is maintained also during non-operation and without air being supplied from the inner region. With an increased air pressure from the inner side, provision can be made for any possibly necessary lubricant not to enter into the inner region.

Another embodiment of the invention makes provision for using a sliding-ring sealing means. At least one sliding ring 62 with a fitting counter-ring 63 makes good sealing possible between the inner region and the outer region. In an advantageous manner, two sliding-ring sealing means are combined with each other so that they form a closed intermediate space between the inner region and the outer region. In an advantageous manner, this intermediate space can then be filled with a sealing medium, or a lubricant, or a cooling medium for the sliding-ring sealing means. This can be supplied through openings 66, and discharged through openings 67. Because an escape of air from the inner space is no longer possible owing to the sliding-ring sealing means, a vent valve 53 is necessary for discharging the supplied air stream 54. An embodiment of this kind having sliding-ring sealing means needs substantially no servicing. Any abraded matter formed may be taken up by the lubricant and discharged. The inner region is protected from contamination even during non-operation and without a supply of air.

Another embodiment of the invention provides for the use of at least one rotary-shaft sealing means. At least one such rotary-shaft sealing means 64 is provided in a gap between the inner region and the outer region. Advantageously two such sealing means are provided in series, so that they define a closed intermediate space which, as already set out above, is filled with or can be supplied with a sealing medium, a lubricant, or a cooling medium. Here too, any abraded matter possibly formed can be carried away by these means. Similarly, here too the inner region is protected from contamination during non-operation and without an air supply.

In another advantageous embodiment of the invention a light-transmitting cover 71 is provided to be firmly attached to the first unit 1. Together with the first unit, this light-transmitting cover seals the light guide 3 from the outer region. Furthermore, for optimal coupling with the light guide 3, at least one optical element is provided that allows free positioning of a light beam path through the light-transmitting cover. The light-transmitting cover may be contaminated in the same way as the unprotected light guide. However, the advantage of the light-transmitting cover is that it may be configured, for example, as a plane surface, and therefore to be easily cleaned. Furthermore, it is of advantage for the light beam passing freely through the light-transmitting cover to be expanded relative to the beam guided in the light guide 3. With this, a transmission remains possible even with single dust and dirt particles deposited on the surface. Furthermore, the optical arrangement for transmission through the light-transmitting cover can be so designed that the light-transmitting cover is disposed outside the focal point, and preferably in a parallel light beam.

In another embodiment of the invention, a dust filter 73, 74 is provided between the first unit and the second unit in the vicinity of at least one gap. The filter tightly seals the gap at least against dust and dirt particles, but allows air to escape from the inside. This embodiment too is sealed from dust and dirt particles during non-operation and without air being supplied. A loaded filter may be easily cleaned from the inside by means of an increased air pressure. The filter preferably consists of a woven fabric such as gauze, but may also be of filter paper. An optimum additional filter 75 has a large capacity and can also filter off coarse contamination.

In another advantageous embodiment of the invention, an additional filter 75 is designed as an electrostatic filter.

Another embodiment of the invention provides for a sealing diaphragm 80 to be disposed on one of the two units in front of a hollow space 81, and adapted to be moved by impaction of the hollow space 81 with vacuum or pressurized air 82. By impaction with pressurized air, the sealing diaphragm can be positioned close to, or urged against, a confronting surface that is preferably assigned to the other unit. By impaction with vacuum, the air is at least partially sucked out of, and the diaphragm drawn into, the hollow space, so that the distance from the opposite surface is enlarged and the sealing means thereby opened. In an advantageous manner, the diaphragm is dimensioned so that in a rest condition it lightly abuts against the opposite surface to achieve a certain minimum sealing in this rest condition. Furthermore, in an advantageous manner a seal is mounted on the opposite surface in order to form a defined seat surface for the sealing diaphragm.

In another arrangement in accordance with the invention, at least one sliding body 2a is provided to serve for accommodating a second light coupler 5. Furthermore, this sliding body is provided with a magnetic bearing means. The magnetic bearing means serves for precise guidance along the light guide 3. It may be designed to be static or also dynamic. Thus, optionally permanent magnets or also electromagnets may be provided to generate the magnetic fields. Furthermore, it is of advantage to provide an additional, preferably electronically controlled position regulating means.

In a method according to the invention for sealing an optical transmission system of the kind under consideration against dirt and dust, the inner region 35 thereof is subjected to an air pressure that is higher than that acting on the outer region 36, so that air streams to the outside through openings in the surface such as gaps, and prevents an entry of particles.

For reasons of clearer illustration, in the previously described embodiments reference was made to air as being representative of any desired gases. Of course, a system according to the invention or a method according to the invention may be put into practice to operate with any desired other gases, preferably nitrogen.

Another system in accordance with the invention comprises an optical rotating data transmission device with a light guide 3 disposed along a circular track along a first unit 1. For the sake of simplicity, only one light guide is described here. Of course, several light guides may be provided in a system according to the invention. For tapping the signals from the light guide 3, a light coupler 5 is provided on a second unit 2 that is supported to be rotatable relative to the first unit 1.

Investigations have shown that abraded particles formed in sliding contact arrangements are attracted by electrically charged objects. This is a consequence of electrostatic charging occurring during the sliding operation. Moreover, owing to the potential to which the contact arrangement is subjected, the particles receive an additional charge.

Therefore, in accordance with the invention a device is provided for electrostatic filtering and/or removing the abraded particles. A device of this kind is furthermore capable of removing also foreign dust and dirt particles. Similarly, an electrostatic device according to the invention can be used to remove the dust from the sliding contact assembly, in order to avoid a deterioration of the insulation.

In an especially advantageous embodiment of the invention, the electrostatic device is designed to be an electrostatic air filter. This comprises at least one electrode that can be subjected to a high voltage. Because very many of the abraded particles are already emitted into the surrounding air where they are distributed in the form of a fine dust, the electrostatic filter arrangement according to the invention is used to filter away the particles that are present in the air and are charged.

Furthermore, in advantageous manner at least one corona electrode is provided that can be subjected to a high voltage and performs a charging of not yet charged particles in the air. This can also be effected by an ionization of the air. The corona electrode is preferably formed to be a thin wire, in order to achieve as high as possible an electric field strength in the vicinity of the electrode.

Another embodiment of the invention makes provision for at least one means for generating an air stream to be present. A means of this kind may be of an active kind, such as a blower or a ventilator. Similarly, this means may also be a means for directing air, such as air guiding plates or air ducts. Of course, both kinds of means may be combined. In many cases of application, simple means for directing air, such as air ducts, are sufficient, because the movement of the second unit relative to the first unit already gives rise to an adequate air stream. It need only be deflected in a correct direction, so that it will preferably first pass the corona electrode and then be guided past the electrode of large area. It is specially expedient to dispose a filter arrangement of this kind together with associated means for controlling the stream ahead of the optical components, so that they receive air that has already been cleaned.

According to the invention at least one blower can be provided for generating an air stream across the contact arrangement, or the light guide 3, or a light coupler 5. With this, the removal of abraded matter away from the contact zone or its surroundings may be further ensured, and the action of the electrode at a distance supported and/or enhanced. The abraded matter is thereby removed in a desired direction by the air stream. Air ducts or air guiding plates may also be provided.

It is of special advantage to combine means for electrostatic air filtering with other, preferably mechanical filters, for example mesh filters or paper filters, in order to achieve a particularly high filtering action.

Another embodiment in accordance with the invention provides for at least one means for taking-up dust and dirt particles to be disposed close to the surface of one of the two units. This means is subjected to high voltage, so that charged dust and dirt particles are attracted. Thus, cleaning of the air streaming through the system is not primarily performed, but rather than this, charged particles are withdrawn from a surface.

Furthermore, it is of advantage for this means to be designed as a rotatable body, preferably a roller. With this, during a movement across the surface of the first or second unit, a clean area of the rotatable body can always be brought into the vicinity of the first or second unit. At the same time, the surface of the rotatable body can be cleaned in a continuous operation. Similarly, the surface of the rotatable body can be recharged with electrical charges in a continuous operation.

In another advantageous embodiment of the invention, at least one of the electrodes consists of a material having a surface on which the abraded particles are highly adherent. Thereby the particles, once attracted thereto, are permanently bound to the electrode, even during a failure of the electrode voltage. Materials of this kind may be, for example, rubber-like materials to which carbon dust adheres well, or other materials such as those used in the form of adhesive tapes.

In another advantageous embodiment of the invention, at least one blower is additionally provided to convey the contaminated air from the contact position to the electrodes. Hereby the abraded material is directed by the air stream towards the electrodes for removal.

In another embodiment of the invention at least one electrode is designed to be a disposable one-way electrode.

As an alternative to this, a part of the filter arrangement can be designed to be an exchangeable one-way component group. Using one-way electrodes or one-way component groups, a rapid and simple exchange of contaminated parts is possible. Similarly, an additional device for cleaning the collecting device or the electrodes may be present, so that a uniform and optimal disposal operation by the at least one electrode may be ensured.

For cleaning the arrangement, according to the invention a removal of deposits from the collecting device may be effected by a device generating mechanical vibrations. Thus, the cleaning operation may be performed automatically and continuously, for example without manual cleaning of components. The abraded particles may be, for example, advantageously collected in a container into which they drop owing to the vibrations. This container may be emptied at large intervals of time. Thus, an elaborate and inconvenient cleaning operation performed on the collecting device itself, or the electrode, or a filter, may be dispensed with.

An advantageous arrangement is obtained when the device for electrostatic removal of dirt and dust particles is mounted to be as close as possible to the sliding contact arrangement at which they originate.

It is of particular advantage for several of the previously described embodiments to be combined with each other in order to achieve an especially high efficiency of the system.

A method according to the invention for removing dust and dirt particles comprises the steps of charging a thin wire at a high voltage and ionizing the air. Furthermore, this is followed by charging a conducting surface to an opposite polarity and directing an air stream past the thin wire and up to the conducting surface on which the dust and dirt particles are deposited.

Another method in accordance with the invention for removing dust and dirt particles, in particular from the surroundings of an optical transmission system, comprises the steps of: charging a roller having a conducting surface by applying a high voltage, rotating the roller with simultaneous movement along a surface to be cleaned. Here this movement is performed at a small distance from the surface. Simultaneously with the movement of the roller, the attracted dust and dirt particles are stripped from the surface of the roller by a stripping means.

The invention claimed is:

1. Optical transmission system for use in a computer tomograph for transmitting modulated optical signals between a first unit and a second unit, the first unit being supported to be rotatable relative to the second unit, comprising:
    a light guide whose longitudinal axis is disposed along a circular track on the first unit;
    at least one first light coupler connected with the light guide for coupling light into or out of the light guide; and
    at least one second light coupler disposed on the second unit to be movable relative to the light guide for coupling light into or out of the light guide, and wherein at least one cleaning unit is disposed on the second unit for removing contaminating matter from a surface of the light guide.

2. Optical transmission system according to claim 1, wherein at least one cleaning unit is connected to the second unit to move along the light guide together with the second unit.

3. Optical transmission system according to claim 1, wherein at least one cleaning unit is provided to be movable along the light guide independently from the second light coupler.

4. Optical transmission system according to claim 1, wherein at least one sensor is provided for detecting contamination of the surface to be cleaned, and is adapted to signal a presence of the contamination to an optional control unit that sets at least one of a duration and an intensity of operation of the cleaning unit in dependence upon an extent of the contamination.

5. Optical transmission system according to claim 1, wherein at least one cleaning unit comprises an appliance for blowing away dust and dirt particles with a nozzle producing a stream of air directed at least onto the light guide.

6. Optical transmission system according to claim 1, wherein at least one cleaning unit comprises a suction appliance having a suction opening through which dust particles and dirt particles are sucked away from the surface of the light guide.

7. Optical transmission system according to claim 1, wherein at least one cleaning unit comprises a brush unit with a brush holder and at least one brush.

* * * * *